United States Patent [19]

Neukum

[11] Patent Number: 5,139,641

[45] Date of Patent: Aug. 18, 1992

[54] METHOD OF GENERATING A CONSTANT DERIVATION POTENTIAL AND A REFERENCE ELECTRODE IN ANALYTICAL CHEMISTRY

[75] Inventor: Alfred Neukum, Gässlesweg 6, 7541 Straubenhardt 1, Fed. Rep. of Germany

[73] Assignee: Alfred Neukum, Fed. Rep. of Germany

[21] Appl. No.: 526,379

[22] Filed: May 18, 1990

[30] Foreign Application Priority Data

May 20, 1989 [DE] Fed. Rep. of Germany ... 8906234[U]
Oct. 27, 1989 [EP] European Pat. Off. ........ 89119963.0

[51] Int. Cl.⁵ .............................................. G01N 27/26
[52] U.S. Cl. ..................................... 204/435; 204/433; 204/153.21; 204/408; 204/414
[58] Field of Search ............ 204/435, 433, 414, 153.21, 204/408

[56] References Cited

U.S. PATENT DOCUMENTS

| | | | |
|---|---|---|---|
| 2,563,062 | 8/1951 | Perley | 324/438 X |
| 3,424,664 | 1/1969 | Severinghaus | 204/435 X |
| 3,463,717 | 8/1969 | Koopman et al. | 204/408 |
| 3,486,997 | 12/1969 | Petersen | 204/435 |
| 4,378,280 | 3/1983 | Dufau | 204/435 |
| 4,818,366 | 4/1989 | Yonco et al. | 204/408 |

Primary Examiner—John Niebling
Assistant Examiner—Bruce F. Bell
Attorney, Agent, or Firm—Darby & Darby

[57] ABSTRACT

In connection with a method for generating a constant derivation potential in analytical chemistry by means of a pH measuring chain containing a reference electrode, in particular for a pH test electrode for use in the meat-processing industry or for measurements in semi-solid substances such as cheese, pastes, in which for carrying out the measurement at least the pH measuring electrode is introduced into the medium to be measured by a corresponding movement, it is proposed that every time the pH measuring electrode is introduced into the medium to be measured, the electrolyte solution of the reference electrode, which is to be brought into contact with the medium to be measured via a diaphragm, be compressed whereby the diaphragm of the reference electrode, which gets into contact at least with the outer surface of the medium to be measured, is subjected to a cleaning action due to the pressure rise in the electrolyte solution occurring simultaneously with such compression.

25 Claims, 2 Drawing Sheets

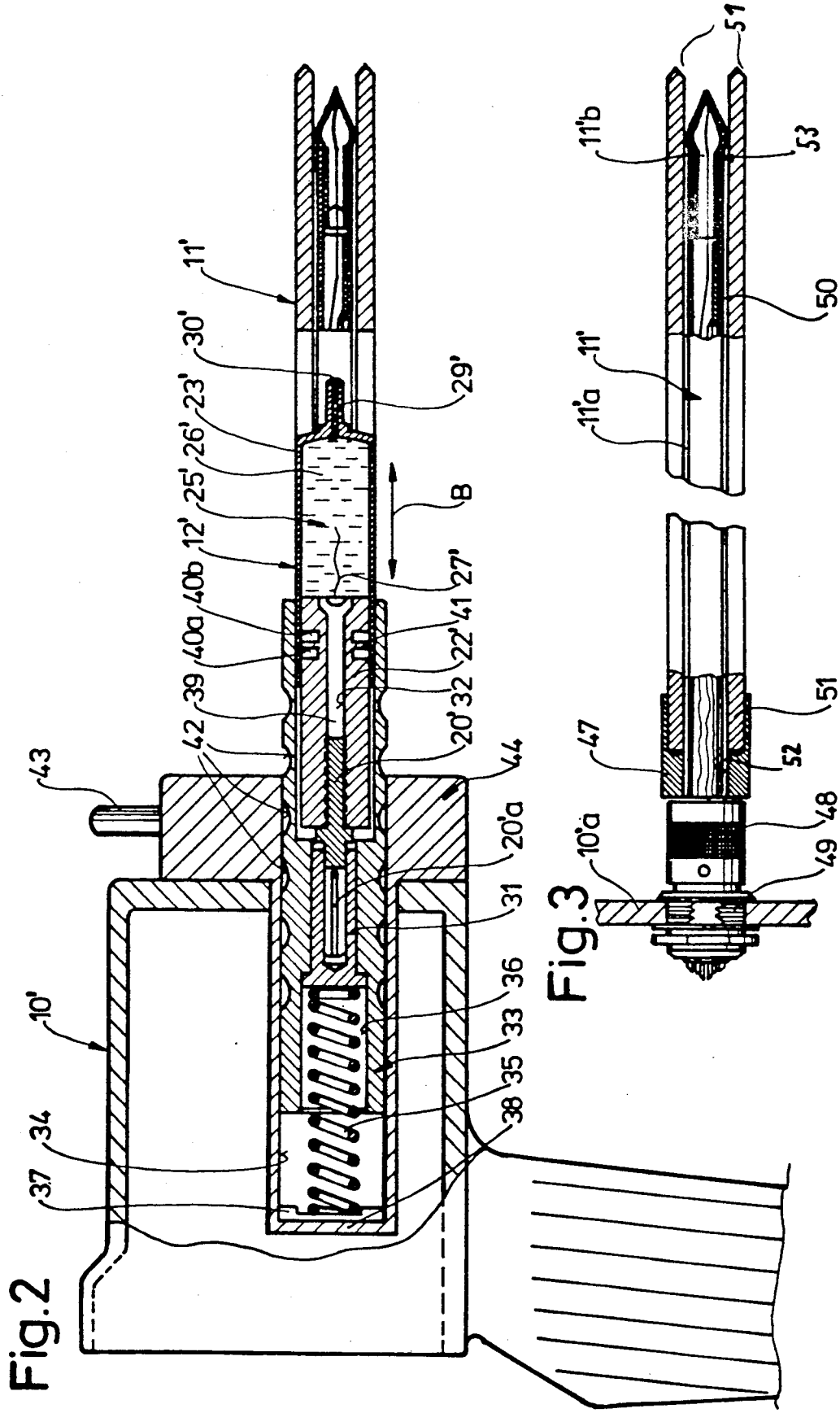

5,139,641

METHOD OF GENERATING A CONSTANT DERIVATION POTENTIAL AND A REFERENCE ELECTRODE IN ANALYTICAL CHEMISTRY

BACKGROUND OF THE INVENTION

The present invention relates to a method for generating a constant derivation potential be means of a reference electrode in analytical chemistry, in particular for a pH measuring chain for use in the meat-producing industry or for measurements in semi-solid substances such as cheese, pastes or the like, in which for carrying out the measurement, at least the pH test electrode is introduced into or brought into contact with the medium to be measured by a corresponding movement.

There have been known a large variety of different measuring arrangements for measuring the pH value by potentiometric means, all of them comprising a glass electrode, a reference electrode and a transducer intended for processing the derivation potentials of both electrodes and for indicating, for example, the pH value so measured.

Most of the pH measuring arrangements consist of a combination of glass electrodes and reference electrodes, thus forming a measuring electrode chain which, when the two electrode types are united in one unit, form a single-point test electrode of the type which is widely in use in industry. The principle of determining the pH value consists in measuring the ion concentration and is largely known so that it need not be described here in more detail. In order to enable the $H^+$ ion concentration to be measured by means of the glass membrane of the measuring electrode and to be converted to a useful pH value, a reference electrode is needed which provides a constant standard or derivation potential for the measuring electrode. The separation at the contact point between the interior electrolyte of the reference electrode and the test solution consists in this case of a capillary connection, the so-called diaphragm.

This design (i.e. a glass membrane in the measuring electrode and a diaphragm in the reference electrode) requires that both the glass membrane and the diaphragm be located in the test fluid during the measuring process. In addition, the diaphragm needs at least one outer contact support.

Problems have been encountered in certain applications, especially in the area of the reference electrode, in connection with measurements carried out, for example, in the meat-processing trade or in semi-solid substances, such as cheese, pastes, or the like. It is of course possible in such cases, too, to introduce the measuring chain into the substance to be measured, to pull it out again upon completion of the measurement and to clean it as required, if the glass membrane of the measuring electrode should have been soiled, but the steps of introducing and withdrawing the measuring chain will necessarily lead to the diaphragm of the reference electrode being soiled or blocked, and this condition will necessarily result in adulterations of the measuring results, maybe even in gradual contamination of the interior electrolyte.

Consequently, it has also been known (DE Utility Patent 87 09 937.3) to equip a pH measuring chain intended for carrying out measurements on such semi-solid substances with a reference system using a gel-like reference electrode in the form of a suitable polymer arranged in an electrolyte vessel of given dimensions. In order to achieve long-term zero-point stability of the reference system, the polymer is enriched with potassium chloride in crystalline form. Further, it is essential that the lower boundary surface of the polymer forming the reference electrode must simultaneously act as a measuring diaphragm which means that the electrolyte vessel may not be closed at this point. During the measuring process, the glass membrane of the pH electrode is then of course introduced into the substance to be measured, but the lower exposed surface of the gel-like reference electrolyte is brought into contact only with the surface of the medium to be measured. The particular physical properties of the polymer provide a self-cleaning effect, and if the design and material of the electrolyte vessel are selected conveniently, there is in addition the possibility to cut off from time to time the worn boundary surface of the diaphragm. If necessary, the reference system and the pH electrode can be detached individually from the handle by which the operator holds the pH measuring chain so formed.

However, it remains a problem of this known pH measuring chain that the measuring diaphragm may deteriorate gradually in the course of the measurement to be carried out, before diaphragm is renewed completely by the radical step of cutting off the lower portion of the reference electrolyte.

Now, it is the object of the present invention to provide a reference electrode, especially for measurements to be carried out on semi-solid substances, which when used in connection with a pH measuring electrode provides zero-point stability and a self-cleaning effect.

Advantages of the invention

The invention achieves this object and provides the advantage that the kinetic energy which is necessary for introducing the pH measuring electrode into the test medium is utilized simultaneously, achieve an instantaneous pressure rise in the arc of the interior electrolyte of the reference electrode which finally has the effect that the electrolyte fluid seeks to escape from the electrolyte chamber through the diaphragm. This instantaneous pressure rise is of particular importance for the present invention. This effect is maintained intentionally for a short time only, the overpressure being balanced out again when the pH measuring electrode is withdrawn from the test medium, for example a semi-solid substance, meat, or the like, so that the loss of interior electrolyte is kept extremely small.

Still, it is rendered possible by the invention, keep the diaphragm—which may, for example, consist of a ceramic pin or of another porous material—absolutely free from contaminations, the only area where electrolyte fluid may get mixed with the substance to be measured being the boundary area between the diaphragm and the test medium. This ensures that diffusion potential errors are reduced to a constant minimum, the flow velocity and the concentration of the electrolyte fluid within the diaphragm remaining practically constant.

Consequently, the reference system used according to the present invention is both zero stabilized and self-cleaning, any dirt particles or other foreign matter which may enter the diaphragm and which might lead to contaminations of the content and to losses being ejected from the diaphragm simultaneously with every measurement by the electrolyte fluid being discharged.

A particularly advantageous embodiment is obtained when the reference electrode is designed in the manner of a piston/cylinder unit in which case the piston is stationary while the role of the moving part is taken over by the cylinder carrying the diaphragm on its forward end, the cylinder being urged back against the piston during introduction into the test medium, so that the inner pressure of the electrolyte of the reference system starts rising.

Another advantageous embodiment of the reference system provides that in order to permit the depth of penetration to be adjusted, with a view to the predetermined longitudinal dimensions of the pH electrode itself, the reference system is adjustable in depth in the common handle or housing, in addition to the relative movement between piston and cylinder, so that even deeper areas of the test medium can be reached by the reference electrode without the reference electrode having to penetrate into the test medium, except perhaps for its projecting diaphragm area. This depth-penetration adjusting feature may, if desired, also permit a finely stepped adjustment.

According to another advantageous feature, additional protective points may be provided in the area of the pH electrode, which may in certain cases have to penetrate into the test medium an important length. The protective points may, preferably, be arranged at uniform peripheral spacings and act to prevent the pH glass electrode, which necessarily forms the forward tip of the measuring electrode, from being unnecessarily stressed mechanically in the area of its membrane. In this case, the design is such that the measuring electrode, together with its metallic electrode tube, the adjoining protective points and the forward pH glass electrode, as well as the reference electrode can be removed from the supporting housing (with its handle) so that the electrodes can be exchanged at low cost in the event one or both of them should fail or be damaged.

Another advantage of the arrangement according to the invention is seen in the fact that in spite of the manual adjustability of the abutment of the reference electrode it is still possible to establish a safe connection, without any risk of rupture, to a cable which as such is subjected to uninterrupted movement. This is achieved by the fact that a biasing spring acting upon the rear end of the supporting or sliding tube for the reference electrode contributes to transmit the constant reference potential supplied by this electrode.

BRIEF DESCRIPTION OF THE DRAWING

Certain embodiments of the invention will be described hereafter in more detail with reference to the drawing in which:

FIG. 2 shows a cross-section similar to FIG. 1 illustrating another embodiment of a pH measuring chain comprising a housing in the form of a gun handle and a reference measuring electrode movably connected therewith;

FIG. 3 is a partial view showing a section through the measuring electrode and illustrating the manner in which it is mounted on the gun handle.

DESCRIPTION OF THE EMBODIMENTS

It is the basic idea of the present invention that the interior electrolyte of the reference electrode is to be subjected to a momentary pressure supporting or effecting its movement to or, if necessary, through the diaphragm every time and only when the pH measuring electrode is introduced into the test medium during use of the pH measuring chain as a whole, and when the area of the reference electrode comes simultaneously to abut against the test medium, mainly against its outside.

Figure 1:
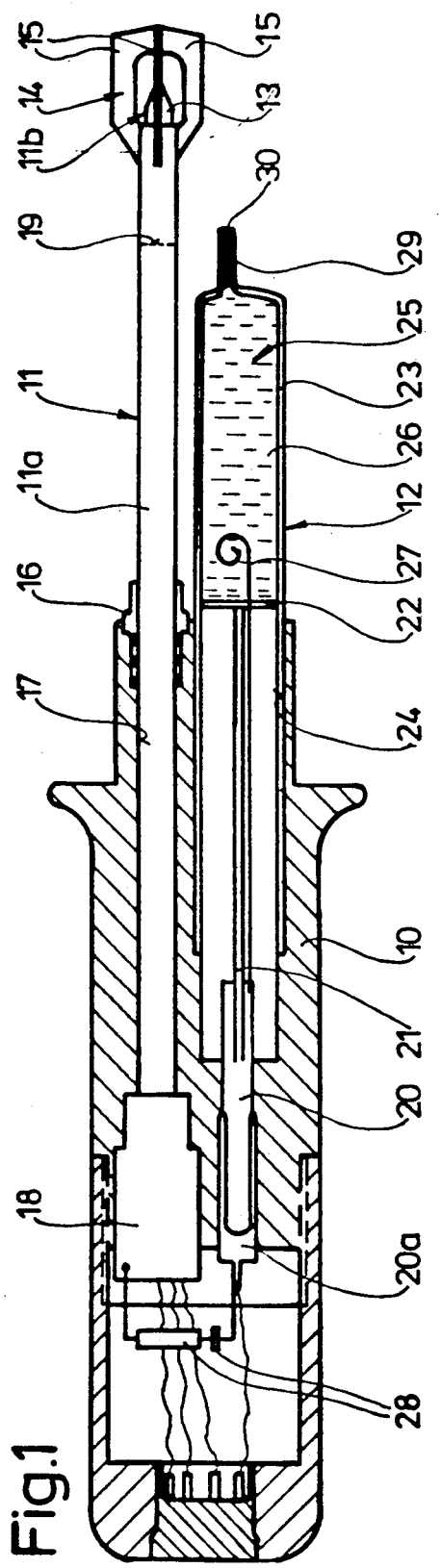
FIG. 1 shows a first embodiment of a pH measuring chain comprising a rod-like handle containing the reference electrode and the measuring electrode in stationary arrangement, with the handle serving as support for the moving cylinder in the area of the reference electrode.

The simpler embodiment of a pH measuring chain with zero-stabilized, self-cleaning reference electrode, as illustrated in FIG. 1, comprises a housing 10 in the form of a handle accommodating and supporting the pH measuring electrode 11 and the reference electrode 12 in its forward portion, i.e. at its right end in the view of FIG. 1. The measuring electrode and the reference electrode are fixed to the handle 10 in this embodiment of the invention, the measuring electrode 11 comprising a, preferably, metallic protective tube 11a supporting in its hollow interior the pH glass electrode insert 11b, with the glass electrode projecting from the protective tube 11a at least by its membrane area 13.

The forward portion of the protective tube 11a may be given the shape of a lancet 14, as illustrated in FIG. 1, for example by providing three wings 15 which project from the forward end of the metallic protective tube 11a, at equal peripheral spacings around the pH glass electrode 11b so as to enclose the latter between them, and which join each other again at the forward end so as to protect the glass insert and the membrane area 13 effectively from damage. The wings 15 may be fixed integrally to the metallic protective tube 11a, for example by welding, and there may also be more than three wings.

The metallic protective tube 11a of the measuring electrode 11 is held in the respective bore 17 of the housing 10 by a suitable screw connection 16. Rearwardly thereof, a contact bushing 18 may be provided for receiving the end of the protective tube 11a with the reference electrode accommodated therein. It goes without saying that the glass electrode insert need not necessarily be guided in the protective tube over its full length, but that instead the insert may end, for example, at the point indicated by the broken line 19 so that the reference electrode may then run back to the contact area through the protective tube, in insulated relationship, in the form of a fine wire.

The reference electrode 12 comprises a piston/cylinder unit of suitable design, the unit being accommodated and supported in the housing 10 in such a way that a relative movement between the piston and the cylinder is obtained in operation of the unit, a feature which will be described in more detail below.

The design of this particular embodiment in such that a piston supporting element 20 which is fixed to the housing, accommodated in an inner bore of the latter, receives and fixes in suitable manner a piston rod 21 carrying a piston 22 on its lower, i.e. its forward end. The piston 22 and the piston rod 21 consist of an electrically non-conductive material, the piston 22 sliding in an electrolyte vessel 23 having the form of a cylinder and being itself accommodated in sliding relationship in a bore 24 of the housing 10.

The space 25 defined by the piston 22 and the inner cylinder walls of the electrolyte vessel 23 contains the electrolyte fluid for the reference electrode, i.e. its interior electrolyte (usually KCl), as indicated at 26 in FIG. 1. The derivation electrode, the electrode insert 27 of the reference electrode, usually a silver/chloride-of-silver conductor, is immersed in the interior electrolyte. The electrode insert 27 is guided, preferably, along the piston rod 21 and may be fixed to the latter; it passes the piston 22 so that its lower end portion is located inside the electrode space. The further electric connection is then effected via the piston mounting 20 located in the housing 10 which may also have the shape of a contact plug.

Preferably, the contact bushing 18 comprises further an integrated electric preliminary amplifier for the pH measuring electrode, for convenient impedance transformation and amplification of the electric measuring signal received from the pH glass electrode 11b. For the purpose of carrying off electric spurious signals, and of shielding the pH measuring electrode 11, the protective tube 11a of the latter may be coupled electrically to the reference electrode by means of decoupling elements consisting of a capacitor and a series-connected resistor 28.

The reference electrode 12 is completed by a narrower longitudinal projection 29 which extends from the forward end of the cylindrical electrolyte vessel 23 in the form of a pipe and which forms the diaphragm, accommodating in its interior a corresponding diaphragm material, for example a ceramic material, a fiber material, or the like, forming the diaphragm 30.

Figure 4:
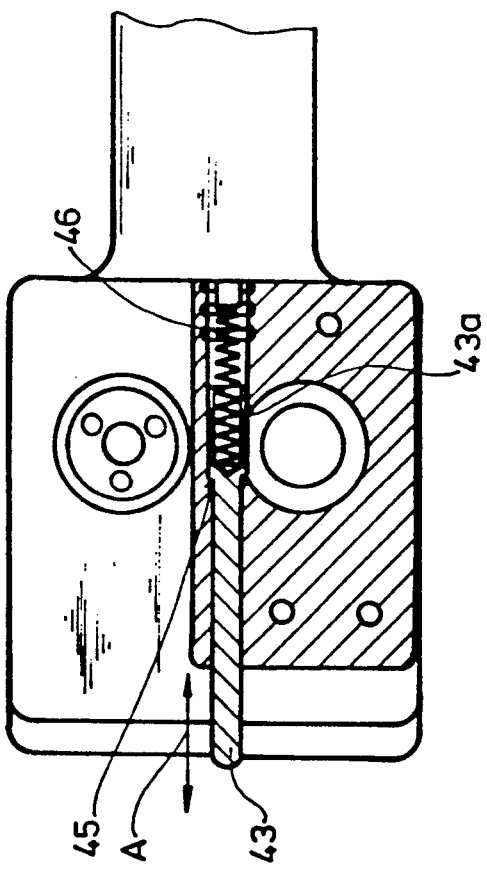
FIG. 4 shows a front view of the embodiment illustrated in FIG. 3, with the electrodes removed, and a section through a sliding support for the reference electrode.

One then obtains the following operation of the pH measuring chain, which is suited for pH measurements in both, liquid and semi-solid substances, especially in the meat-processing trade, it being understood that the following description applies by analogy also to the second modified embodiment of a pH measuring chain as illustrated in FIGS. 2 to 4.

Holding the pH measuring electrode 11 by the handle of the housing 10, one introduces it into the (semi-solid) substance to be measured, or presses it against the surface of the latter, for example if skin values are to be measured using a flat membrane, until the forward end of the diaphragm 30 is in contact with the surface of the medium to be examined. The manual force which is exerted via the handle upon the reference electrode 12 or the latter's diaphragm 30, during introduction of the pH measuring chain, when the diaphragm 30 gets into contact with the medium under examination, produces a force acting upon the cylinder of the movable electrolyte vessel which tends to urge the cylinder back, whereby at the same time safe physical and electric contact is established in the diaphragm area of the reference electrode.

The piston rod 21, together with its piston 22, being fixed in the handle, an overpressure builds up in the electrolyte vessel 25 so that the electrolyte fluid 26 seeks to escape through the diaphragm 30 which, as any other diaphragm, has of course a porous structure.

This has the effect that mixing of the electrolyte fluid with the test medium will occur exclusively at the forward boundary surface between the diaphragm 30 and the test fluid, while no such mixing will occur within the diaphragm, not to speak of the area of the interior electrolyte. This leads to a self-cleaning effect in the area of the diaphragm, combined with safe zero stabilization, as any diffusion potential errors can be reduced in this manner to a constant minimum and the flow velocity and concentration of the electrolyte fluid in the diaphragm will remain practically constant during the measurement. In addition, particles of any origin that may enter the diaphragm, such as dirt particles or particles of the test medium, will be ejected from the latter through the electrolyte fluid being discharged under the action of the "measuring pressure".

Upon completion of the measuring process, the pH measuring chain is withdrawn from the substance to be measured so that the overpressure prevailing in the electrolyte chamber 25 is balanced out as a result of a corresponding slight compensating movement of the electrolyte vessel.

Another advantage of the longitudinal projection, which extends in forward direction by a given length and which carries the diaphragm 30, lies in the fact that the diaphragm 30 can be cleaned easily, if this should prove necessary, for example by scraping it clean. Or else the diaphragm can be shortened a little by cutting or filing.

Considering that the second embodiment illustrated in FIGS. 2, 3 and 4 is based on similar basic principles, comparable components will be identified in the following description by the same reference numerals, supplemented only by an apostrophe.

As can be seen best in the representation of FIG. 2, the electrolyte vessel 23' of the reference electrode 12' is comparable with the cylinder design of the electrolyte vessel according to FIG. 1 and is also equipped with a forward longitudinal projection 29' with a diaphragm 30' accommodated therein.

However, the piston 22' has a somewhat larger volume and is held in position by a supporting element 20' similar to a banana plug, which engages a stationary contact bushing 31 by a longitudinal plug element 20a' provided on its side facing away from the piston. The other side of the supporting element 20' of the piston is provided with a projection engaging a bore 32 in the piston 22'.

Here, too, the electrode insert 27 passes through the piston 22', along its inner bore 32, ending in the electrolyte chamber 25'.

The arrangement differs from the embodiment of FIG. 1 by the fact that the reference system in its entirety can be adjusted in depth within the gun-like housing 10' of the handle. The arrangement includes for this purpose a sliding pipe 33 which accommodates and supports the piston/cylinder unit 22', 23' and which itself is also accommodated in sliding relationship, similar to a piston, in a receiving bore 34 formed by the housing 10'. This arrangement allows the penetration depth for the reference system 12' to be adjusted, a feature which is particularly convenient in cases where the sensitive area of the measuring electrode is to reach different depths of the test medium, for example if different tissue layers are to be tested during meat examinations. In order to insure that the reference system will in such cases, too, get into contact only with the outer surface of the substance under examination, the reference system can be adjusted in depth in its entirety, in addition to the relative adjustment in the area of the electrolyte vessel serving to increase the pressure of the interior electrolyte, which latter is also possible in the case of the embodiment described first. For the purpose of this depth adjustment, the sliding pipe, which now supports the reference system instead of the housing, can be introduced into, and conveniently also locked in, the receiving bore 34 of the housing in different positions.

First of all, there is provided a compression spring in the form of a biassing spring 35 seated in a recess 36 of the sliding pipe 33 and bearing upon the rear end of the receiving bore 34 of the housing 10', at the contact plate 37 for the reference system provided in this position. This is a suitable arrangement because the biassing spring 35 extends right to the end face of the contact bushing 31 so that it is in a position, due to its firm contact on both ends, to transmit the derivation potential of the reference system to the contact plate 37 from where it is then transmitted, in a suitable manner, via a connection wire 38 to the processing circuit arranged in the gun-handle housing 10'.

The silver—chloride-of-silver wire 27' of the reference electrode may be guided into the electrically conductive piston supporting element 20' along the inside of the piston and through a suitable epoxy seal 39, in which case an improved sealing effect may be achieved by two annular grooves 40a, 40b provided in the forward area of the piston 22', with an axially resilient sealing element 41 engaging such grooves, similar to the arrangement of a medical syringe, whereby perfect sealing of the electrolyte chamber from the outside can be achieved.

To enable the reference electrode system to be locked in position, different means may be provided, for example an inwardly projecting and manually operable spring element engaging successive notches in the sliding pipe, like a catch, so that the sliding pipe is locked against the action of the biassing spring 35. Preferably, the outer periphery of the sliding pipe 33 is provided with wave-like annular recesses 42, as shown in FIG. 2, extending around the cylindrical shape of the sliding pipe so as to reduce the latter's diameter over certain sections.

These annular recesses 42 of the sliding pipe coact with a pin 43 fixed to the housing and projecting into the recesses from the outside. It may be convenient to have the pin 43 supported in a partial housing 44 of its own, which may be attached to the gun handle of the housing 10' and screwed to the front of the latter, and which may be provided with a rearwardly projecting protuberance, as viewed in FIG. 2, constituting the pipe with the receiving bore 34 for the sliding tube.

The locking pin 43 can be displaced upwardly and downwardly in its partial housing 44, as indicated by double arrow A in FIG. 4, and comprises a lower thicker portion 43a which is separated from an outwardly projecting, narrower portion of the locking pin 43 by a shoulder 45.

In the upper end position, which is brought about by the biassing force of a compression spring 46, the thicker portion 43a of the locking pin 43 fits exactly in one of the annular notches 42 in the sliding tube 33 of FIG. 2 so as to lock the latter in both axial directions.

When pressure is exerted upon the locking pin 43 from above, then the locking pin 43 will move downwards, against the action of the spring 46, until the thinner portion only of the locking pin 43 is present adjacent the annular notches 42 of the sliding tube. It is then possible to pull the sliding tube vertically past the thinner portion of the locking pin 43 in the direction indicated by double arrow B in FIG. 2, into any desired end position, and to lock it in this position by releasing the locking pin 43.

It will be recognized immediately, in view of this mechanism, that the reference system can easily be detached completely from the handle so that nothing else but the spring will remain in the housing, maybe fixed to the contact plate 37, which permits the reference system to be exchanged without any problems.

Similarly, the pH measuring electrode, which is illustrated once more in FIG. 3, can be easily detached from the unit in the case of this embodiment of the invention. It has been necessary to illustrate this detail separately because the measuring electrode is partly hidden behind the reference system in the view of FIG. 2.

The basic structure of the measuring electrode 11' with its protective tube 11a' and the forward glass electrode insert 11b' may be as described before with reference to FIG. 1, except that the protective tube 11a' is fixed to the electrode plug 48 and that the latter is received by an electrode bushing 49 which passes through the housing wall 10a' and is screwed to the latter. It is thus possible to separate the measuring electrode system 11' at the separating point formed by the electrode plug 48 and the electrode bushing 49, for which purpose the plug-in connection may be provided with snap-in means of a suitable design, provided for example in peripheral distribution and holding the plug securely in the receiving bushing 49 in axial direction. If desired, one may also provide contacts (pins and sockets) arranged coaxially to each other for transmitting the derivation potential.

According to another advantageous variant of this embodiment of the invention, an additional temperature sensor 50 is arranged inside the protective tube 11a' of the measuring electrode 11', which makes it possible, without great expense, to supply the impedance transformer and calculating unit in the housing of the gun handle with an additional temperature signal which can then be included in the calculations and be taken into account for the measured pH values indicated directly at the housing. The supply lines leading to the temperature sensor 50, which may for example be a Pt-1000 element, are likewise accommodated inside the protective tube 11a'.

Another variant provides that instead of giving the glass electrode a lancet-type design and enclosing it by the protective tube, as illustrated in FIG. 1, the whole pH electrode protective tube, including the forward glass electrode, may be surrounded by protective points 51 projecting also beyond the forward point of the glass electrode, i.e. beyond its membrane area. These protective points are seated in a mounting 47 arranged in the area of the electrode plug 48, the mounting being connected to the protective tube 11a' in a suitable manner. Preferably, three such protective points 51 are provided, at uniform angular spacings, and arranged around the protective tube and the glass electrode mounted in the latter, for example embedded in putty. The protective points 51 are firmly retained in the mounting 47, adjacent to the protective tube. The mounting 47, together with the protective points, can be detached separately by a thread 52 provided on the protective tube 11a'. This provides the advantages that the system can be cleaned more easily, that the unit can be operated with a single perforation hole, though then with unprotected pH membrane, and that when exchanging the pH electrode it is not necessary to change the mounting and the protective points as well.

There is still another circumstance which is worth noting. The pH membrane and/or the area of the forward point of the pH glass membrane are curved outwardly/rearwardly whereby a smooth transition is obtained between the glass membrane and the protective tube, as indicated at 53 in FIG. 3. This provides several advantages, namely that no dirt trap is obtained in the transition area, that the membrane is supported at its rear, that elastic embedding and sealing can be selected, and that the different coefficients of expansion of glass and steel (protective tube) remain without effect.

All features described by the specification and the following claims and illustrated in the drawing may be essential to the invention individually or in any combination thereof.

I claim:

1. A reference electrode for a measuring chain for carrying out analytic chemical measurements of a substance, a said reference electrode, for generating a constant derivation potential during measurement, having a chamber therein for storage of an electrolyte solution, said chamber including porous means through which said electrolyte solution may pass, and compression means for elevating the pressure of said electrolyte solution in response to said engagement of said reference electrode with said substance.

2. A reference electrode as in claim 1 and further comprising a pH measuring electrode for determining a chemical condition of said substance after said measuring electrode is engaged with said substance.

3. A reference electrode as in claim 1, wherein said chamber includes a hollow cylinder closed at one end by a slideable piston, and at its other end by said porous means, said piston and cylinder comprising said compression means, and further comprising a housing serving as a handle, said piston being fixed relative to said housing, said cylinder being slideable in said housing relative to said piston;

engagement of said porous means causing said cylinder to move relative to said piston and compress said electrolyte solution in said chamber, whereby the pressure of said electrolyte solution is increased.

4. A reference electrode according to claim 2, wherein said pH measuring electrode is mounted in stationary relationship to said housing, said pH measuring electrode comprises an electrically conductive protective tube carrying at its forward end a pH glass electrode insert which is protected, together with a glass membrane, by surrounding protective means.

5. A reference electrode according to claim 2, wherein said pH measurement electrode and said reference electrode are arranged in separate housings each forming a handle.

6. A reference electrode according to claim 2, wherein protective means provided for said pH measuring electrode completing said pH measuring chain includes an at least two-edged lancet a glass electrode insert.

7. A reference electrode according to claim 4, wherein said electrically conductive protective tube of the said pH measuring electrode is connected to the potential of said reference electrode via a coupling capacitor connected in series to a resistor.

8. A reference electrode according to claim 3, wherein a sliding tube, in which said piston and cylinder unit and said electrolyte chamber are seated, can be adjusted to different depth positions in said housing for the purpose of adjusting the penetration depth of the adjacent pH measuring electrode.

9. A reference electrode according to claim 8, wherein said sliding tube is seated in a receiving recess of said housing and can be locked therein and includes a bore accommodating in sliding relationship the cylinder forming said electrolyte chamber for the reference system, said piston, held in stationary relationship in said sliding tube by means of a piston supporting element, being arranged to slide in said cylinder.

10. A reference electrode according to claim 9, wherein the outer periphery of the said sliding tube includes one of annular grooves and notches subject to engagement by a locking pin securing said sliding tube in both axial directions, as required for the desired depth adjustment.

11. A reference electrode according to claim 10, wherein said locking pin is accommodated in a separate partial housing which is attached to said housing designed in the form of a gun handle, said partial housing being provided with an inwardly directed protuberance forming the receiving bore for said sliding tube, and said locking pin being movable in a direction perpendicular to the sense of adjustment of said sliding tube, against the action of a biassing spring.

12. A reference electrode according to claim 11, wherein in the extended rest position of said locking pin a thicker portion of the locking pin engages one of said annular grooves of said sliding tube and can be moved out of the respective annular groove by pushing it down manually, said sliding tube being released for axial depth adjustment of the reference system.

13. A reference electrode according to claim 3, wherein an electrode insert in the form of a wire extends through said piston and along a piston rod carrying the piston up to a rear piston mounting element which is fitted, in the manner of a bushing insert, in a contact bushing mounted stationarily in said housing designed in the form of a longitudinal handle.

14. A reference electrode according to claim 13, wherein said wire, which is immersed in the interior electrolyte, extends through a channel in the cylindrical longitudinal piston in a sealed relationship, up to said piston mounting element, said mounting element having a two-sided plug-like design and is mounted in an electrically conductive manner, and the piston mounting element carries said piston on a forward extension while its rearward end is inserted in a receiving bushing accommodated in said sliding tube.

15. A reference electrode according to claim 14, wherein said receiving bushing ends in a rearward recess of said sliding tube, which recess accommodates a biassing spring which on one end is conductively connected to said receiving bushing while its opposite end engages a contact plate of said receiving bore of the housing so that the electric connection is established via said biassing spring.

16. A reference electrode according to claim 2, wherein said pH measuring electrode is surrounded by at least two protective points held in a mounting element which can be detached from said protective tube to which it is connected, said points projecting beyond the forward end of said glass electrode insert, thus surrounding and protecting the latter.

17. A reference electrode according to claim 16, wherein said mounting element for said protective points and the electrode shaft are connected to an electrode plug held in detachable, lockable and self-locking relationship in an electrode bushing fixed to the housing so that both said pH measuring electrode and said reference electrode can be detached from said housing for replacement, cleaning and maintenance purposes.

18. A reference electrode according to claim 2, wherein a temperature sensor is arranged in said a protective tube of said measuring electrode, and connection contacts of said temperature sensor are run to processing circuits in a housing via an electrode plug/electrode bushing combination.

19. A reference electrode according to claim 2, wherein said porous means is received in a forward tubular longitudinal portion of said cylinder forming said electrolyte chamber and includes a ceramic insert of porous material.

20. A reference electrode according to claim 3, wherein a tubular extension accommodating said porous means is an integral, thinner portion of said cylinder so that supplementary cleaning and clearing of said porous means can be effected by one of scraping off and shortening the length of the longitudinal projection.

21. A reference electrode according to claim 3, wherein sealing of said piston from the inner cylinder wall, in which said piston is accommodated in sliding relationship, is effected by a double annular notch in the piston, said notch accommodating a freely movable, sealing annular tongue projecting peripherally.

22. A reference electrode according to claim 2, wherein a pH glass electrode insert of said measuring electrode is bulged outwardly to avoid trapping dirt and to provide an additional rear support for said insert.

23. A method for providing a reference potential in an electro-chemical measuring device having a reference electrode of the type having an electrolyte chamber containing electrolyte solution, said chamber having porous means through which said electrolyte may pass, comprising the steps of:

moving said reference electrode into contact with the substance to be measured, and increasing the pressure on said electrolyte upon contact of the porous means with the substance to be measured to cause said electrolyte to flow outwardly from the chamber through said porous means to the substance to be measured, whereby said porous means is subjected to a self-cleaning action during each use thereof.

24. A method as in claim 23, and further comprising the steps of:

removing said reference electrode from said medium to be measured after measurements are made; and reducing said electrolyte solution pressure substantially concurrently with removal of said reference electrode from said medium.

25. A method as in claim 23, wherein said measuring device is for pH measurement, said electrolyte solution is KCl and said porous means is a diaphragm.

* * * * *